US011065958B2

(12) United States Patent
Mestha et al.

(10) Patent No.: US 11,065,958 B2
(45) Date of Patent: Jul. 20, 2021

(54) CONTROL SYSTEM AND METHOD

(71) Applicant: General Electric Company, Schenectady, NY (US)

(72) Inventors: Lalit Keshav Mestha, Niskayuna, NY (US); James Brooks, Schenectady, NY (US); Peter Tu, Niskayuna, NY (US)

(73) Assignee: TRANSPORTATION IP HOLDINGS, LLC, Norwalk, CT (US)

( * ) Notice: Subject to any disclaimer, the term of this patent is extended or adjusted under 35 U.S.C. 154(b) by 444 days.

(21) Appl. No.: 15/397,469

(22) Filed: Jan. 3, 2017

(65) Prior Publication Data

US 2018/0186234 A1 Jul. 5, 2018

(51) Int. Cl.
| | |
|---|---|
| *A61B 5/18* | (2006.01) |
| *B60K 28/06* | (2006.01) |
| *G06K 9/20* | (2006.01) |
| *G06K 9/00* | (2006.01) |
| *H04N 7/18* | (2006.01) |

(Continued)

(52) U.S. Cl.
CPC .......... *B60K 28/066* (2013.01); *A61B 5/0077* (2013.01); *A61B 5/0205* (2013.01); *A61B 5/18* (2013.01); *G06K 9/00255* (2013.01); *G06K 9/00268* (2013.01); *G06K 9/00315* (2013.01); *G06K 9/00845* (2013.01); *G06K 9/209* (2013.01); *G06K 9/2018* (2013.01);
(Continued)

(58) Field of Classification Search
CPC ...... B60K 28/02; B60K 28/06; B60K 28/066; B60W 2040/0818–0872; B60W 40/08; B60W 40/09; B60W 50/14; B60W 50/16; B60W 2050/143; B60W 2050/146; G06K 9/00845; A61B 5/18
See application file for complete search history.

(56) References Cited

U.S. PATENT DOCUMENTS

| | | | |
|---|---|---|---|
| 5,729,619 | A | 3/1998 | Puma |
| 6,822,573 | B2 | 11/2004 | Basir et al. |

(Continued)

FOREIGN PATENT DOCUMENTS

| | | |
|---|---|---|
| CN | 1784701 A | 6/2006 |
| CN | 1910593 | 2/2007 |

(Continued)

OTHER PUBLICATIONS

Alldieck et al., "Context-Aware Fusion of RGB and Thermal Imagery for Traffic Monitoring", MDPI Sensors, 2016 (Year: 2016).*

(Continued)

*Primary Examiner* — Spencer D Patton
(74) *Attorney, Agent, or Firm* — Josef L. Hoffmann; The Small Patent Law Group, LLC (57) ABSTRACT

A control system having one or more controllers configured to determine physical or psychophysiological (3P) changes of an operator of a vehicle. First and second imaging devices take real-time images of an operator of a vehicle. Then, based on the physical, physiological and/or psychological features extracted from the imaging device data, and a 3P model from historical data the one or more processors also configured to, responsive to the physical, physiological and/or psychological changes of the operator of the vehicle, alert the operator and control the operation of the vehicle.

21 Claims, 4 Drawing Sheets

(51) Int. Cl.
*A61B 5/0205* (2006.01)
*A61B 5/00* (2006.01)
*A61B 5/318* (2021.01)
*A61B 5/369* (2021.01)

(52) U.S. Cl.
CPC .............. *H04N 7/181* (2013.01); *A61B 5/318* (2021.01); *A61B 5/369* (2021.01)

(56) References Cited

U.S. PATENT DOCUMENTS

| | | | |
|---|---|---|---|
| 6,927,694 | B1 | 8/2005 | Smith et al. |
| 6,946,966 | B2 | 9/2005 | Koenig |
| 8,698,639 | B2 | 4/2014 | Fung et al. |
| 8,952,819 | B2 | 2/2015 | Nemat-Nasser |
| 2005/0024212 | A1 | 2/2005 | Hultzsch |
| 2007/0008151 | A1 | 1/2007 | Victor et al. |
| 2009/0261979 | A1 | 10/2009 | Breed et al. |
| 2010/0191124 | A1* | 7/2010 | Prokoski .............. A61B 5/0064 600/473 |
| 2010/0222687 | A1 | 9/2010 | Thijs et al. |
| 2012/0212353 | A1* | 8/2012 | Fung ...................... B60K 28/06 340/905 |
| 2016/0272217 | A1* | 9/2016 | Kim ..................... B60K 28/066 |

FOREIGN PATENT DOCUMENTS

| | | | |
|---|---|---|---|
| CN | 102902874 | A | 1/2013 |
| CN | 104584084 | A | 4/2015 |
| CN | 104732251 | A | 6/2015 |
| CN | 104973054 | A | 10/2015 |
| DE | 3826943 | A1 | 2/1990 |
| EP | 1788536 | * | 5/2007 .............. A61B 5/18 |
| GB | 2465439 | A | 5/2010 |
| JP | 2008223879 | A | 9/2008 |
| KR | 2015007536 | A | 1/2015 |
| WO | 2006000166 | A1 | 1/2006 |
| WO | 2015174963 | A1 | 5/2014 |
| WO | 2015066445 | A1 | 5/2015 |
| WO | 2015175435 | A1 | 11/2015 |
| WO | 2016044678 | A1 | 3/2016 |

OTHER PUBLICATIONS

Sinha et al., "Real Time Implementation for Monitoring Drowsiness Condition of a Train Driver using Brain Wave Sensor", International Journal of Computer Applications, Apr. 2016, 6 Pages, vol. 139—No. 9.

Shahid Maqbool, "Driver drowsiness detection—The technology race in the car to keep the driver awake and focused", Blog, Tape Daily.

Azim Eskandarian et al. "Drowsy and Fatigued Driving Problem Significance and Detectioin Based on Driver Control Functions", Handbook of Intelligent Vehicles, Springer-Verlag London Ltd. 2012, pp. 941-974.

Shende et al., "Driver Fatigue Detection System and the Status Transmission", International Journal of Innovative Research in Science, Engineering and Technology, Jun. 2015, vol. 4, Issue 6.

* cited by examiner

CONTROL SYSTEM AND METHOD

FIELD

The subject matter described herein relates to monitoring a vehicle operator, and to a control system for responding to monitored parameters.

BACKGROUND

Operators of heavy duty vehicles have a major responsibility in operating the vehicles to prevent accidents that can harm passengers and bystanders causing major harm. In an effort to combat operator errors due to work-load fatigue, some modern vehicles (e.g., locomotives) incorporate a switch called an 'alerter'. This switch enables monitoring of operator alertness by forcing the operator to periodically actuate an alert button to send a response to the system to indicate attentiveness.

Another system provides operator alertness detection technology by requiring some input from the operator every designated distance traversed by the vehicle (e.g., ~1100 meters), or else a penalty brake is applied to stop movement of the vehicle. Standards for this style of alerter have been required of all passenger and freight locomotives operating above 25 miles per hour (mph), or approximately 40 kilometers per hour (kph) by the Federal Railroad Administration (FRA) since 2012. Additionally, this alerter may require the operator to consider a simple "cognitive alerter" where the operator must answer basic math questions.

Another system attempts to predict the alertness of a vehicle operator using sleep schedule and performance data related to the operator. The system uses three different psychological processes; effects of time awake, circadian process, and sleep inertia to predict the alertness of the operator.

While these types of systems ensure an operator has not become completely incapacitated, the systems impede operator workflow and are considered annoying by many operators. Additionally, these systems are unable to account for monitoring operator behavior that is indicative of potential dangerous operating conditions. This includes monitoring for signs of operator fatigue, monitoring operator health conditions or monitoring to ensure the operator is not being distracted by electronics or other distractors while operation of the vehicle is occurring.

BRIEF DESCRIPTION

In one embodiment, a control system is provided. The control system has one or more processors configured to determine physical changes of an operator of a vehicle without requiring intervention of the operator. The one or more processors are also configured to, responsive to the physical changes of the operator of the vehicle that are determined indicating that the operator is inattentive to control of the vehicle, alert the operator.

In one embodiment, a method is provided related to monitoring a control system with operator in the control loop. Steps include determining physical changes of an operator of a vehicle and responsive to the physical changes of the operator of the vehicle that are determined indicating that the operator is inattentive to control of the vehicle, alerting the operator with an alarm.

In one embodiment, a control system is provided with one or more controllers configured to monitor physical changes of the operator of the vehicle. The one or more processors are also configured to, responsive to the physical changes of the operator of the vehicle that are determined indicating that the operator is inattentive to control of the vehicle, brake the vehicle.

DETAILED DESCRIPTION

A control system has one or more processors that are configured to provide a fully contactless imaging system and a physical and psychophysiological (3P) model for estimating operator parameters and conditions including fatigue and drowsiness in real-time. The imaging system includes a first imaging device that typically is an RGB (Red Blue Green) digital camera, that can be a RGBD (Red, Green, Blue, Depth) camera, and a second imaging device that typically is a thermal camera that both provide data to the one or more processors for creating a physically and psychophysiologically output of the operator in real-time. The one or more processors utilize the data from the RGB camera and thermal camera to passively measure bio-signals emanated, including an operator's face during night or day while the operator is on the job, without asking the operator to indicate vigilance periodically. Thus, the control system is usable during the day or night without additional illuminators depending on imaging device types inside the operator's cabin or surrounding environment, or electrodes affixed to the skin. As a result, this allows for long monitoring functions unobtrusively inside the vehicle.

The first imaging device, while described as a RGB camera, may be of any type, including but not limited to a reflected near infrared (NIR) camera or a shortwave infrared (SWIR) camera. The RGB, NIR and SWIR cameras may be instrumented with suitable illuminators. Similarly, the second imaging device, while described as a thermal camera may of any type, including but not limited to a midwave infrared (MWIR) or a longwave infrared (LWIR) camera which is capable of collecting emitted waves. Other imaging devices of interest suitable for this kind of alerter is ultra-wide band microwave imaging technology. Depth measuring imaging devices such as Kinect, Multi and hyperspectral cameras in the visible and infrared wavelength range are other imaging devices suitable for use in the alerter technology. Any combinations of these imaging devices may be used to extract 3P information about the operator intervention.

Historical data related to physical, physiological or psychophysiological (3P) parameters of the operator in the form of a 3P model is generated through experimentation to be used by the control system. A 3P model is a relationship between features (or indicators) from non-contact sensor data to cognitive indicators derived from body-worn sensor(s) data responsible for fatigue and alertness. During experiments, a imaging system provides data related to visible physical characteristics (i.e., physical indicators) of the operator. These include, but are not limited to, sagging posture, leaning of head, head nods, gaze direction, expressions, eye-ball motions, pose, gestures, blinking, yawning, and the like.

During experiments, psychophysiological indicators such as pulse rate, respiration rate, heart rate variability, peak-to-peak pulse locations, power in harmonics, knowledge-based/shallow/deep learning features are generated from blood flow data coming from below the skin and can be measured using imaging devices as well as with body-worn devices well-known to the medical community, including: electroencephalographic (EEG), photoplethysmographic (PPG), videoplethysmographic (VPG), electrocardiographic (ECG), ballistocardiographic (BCG), electromyographic (EMG), phonocardiographic (PCG), galvanic skin response (GSR), transcranial Doppler (TCD) sonography, and functional near infrared (fNIR) signals.

During experiments conducted offline in a controlled setting, data from body-worn devices is used not only to validate the measurements from non-contact imaging-based systems, but also are used to extract well-known psychological indicators such as fatigue and drowsiness from EEG signals. Physical characteristics (i.e., physical indicators) are largely associated with the above surface indicators, and can be obtained with imaging devices such as RGB and/thermal imaging device. Combining a subset of both measurements in one device has the potential to provide very accurate results.

While these experiments are occurring the corresponding 3P changes detected by the imaging devices are compared to the psychological parameters that are measured and collected in the form of fatigue and drowsiness. Mathematical modeling is then utilized to construct a 3P model that associates the images and data from images generated by one or more imaging systems (e.g., features) to the corresponding psychological effects experienced by an operator. Health effects of the operator are obtained from measurements such as pulse rate, respiration rate, peak-to-peak pulse locations, and the like. The control system utilized on the vehicle is then able to detect physical and physchophysiological (3P) changes of an operator using a 3P model based on the images which is developed from human experiments in a controlled laboratory setting. These 3P changes are monitored in real-time without requiring intervention by the operator.

For example, the 3P changes of the operator may be monitored without requiring the operator to actuate a button or switch, provide an answer to a query or test, keep weight on a kill switch, or the like. Because images from the imaging devices contain health parameters, they are also monitored over time. In this manner health parameters as well as psychological parameters, fatigue and drowsiness, are measured unobtrusively and without operator intervention over time or at regular intervals or as and when required while operating the train. In particular, the control system takes data generated and utilizes an algorithm or look up tables to determine the health parameters of the operator. In this manner, the control system is a contactless and a passive monitoring system with abilities to record 3P data of the operator inside the cabin at all times without additional illumination depending on the type of imaging device used.

The control system allows predictive capabilities to be incorporated to provide early warning of impending danger to a vehicle such as a locomotive as a result of operator error. Additional performance hindering behavioral states such as texting, operational compliance functions, and situational awareness external to the cabin is recognized from image analytics and combined with 3P quantities to provide more advanced capabilities. In addition, the control system can be used to perform postmortem analysis in the event of accidents.

The control system is unobtrusive and based on physiological cues rather than only behaviors as indicated by physical characteristics, and uses task-relevant knowledge of expected behaviors and workload. The system measures psychological data that includes data related to fatigue and drowsiness and other operator based parameters with advanced capabilities. For example, with highly sensitive thermal imagery of the operator's face, one can extract additional information associated with psychophysiology (e.g., emotion, joy, arousal etc.) by monitoring thermal changes in regions such as nose, cheeks, periorbital/supra-orbital regions, forehead, maxillary, neck-carotid, lips/mouth and the like.

Figure 1:
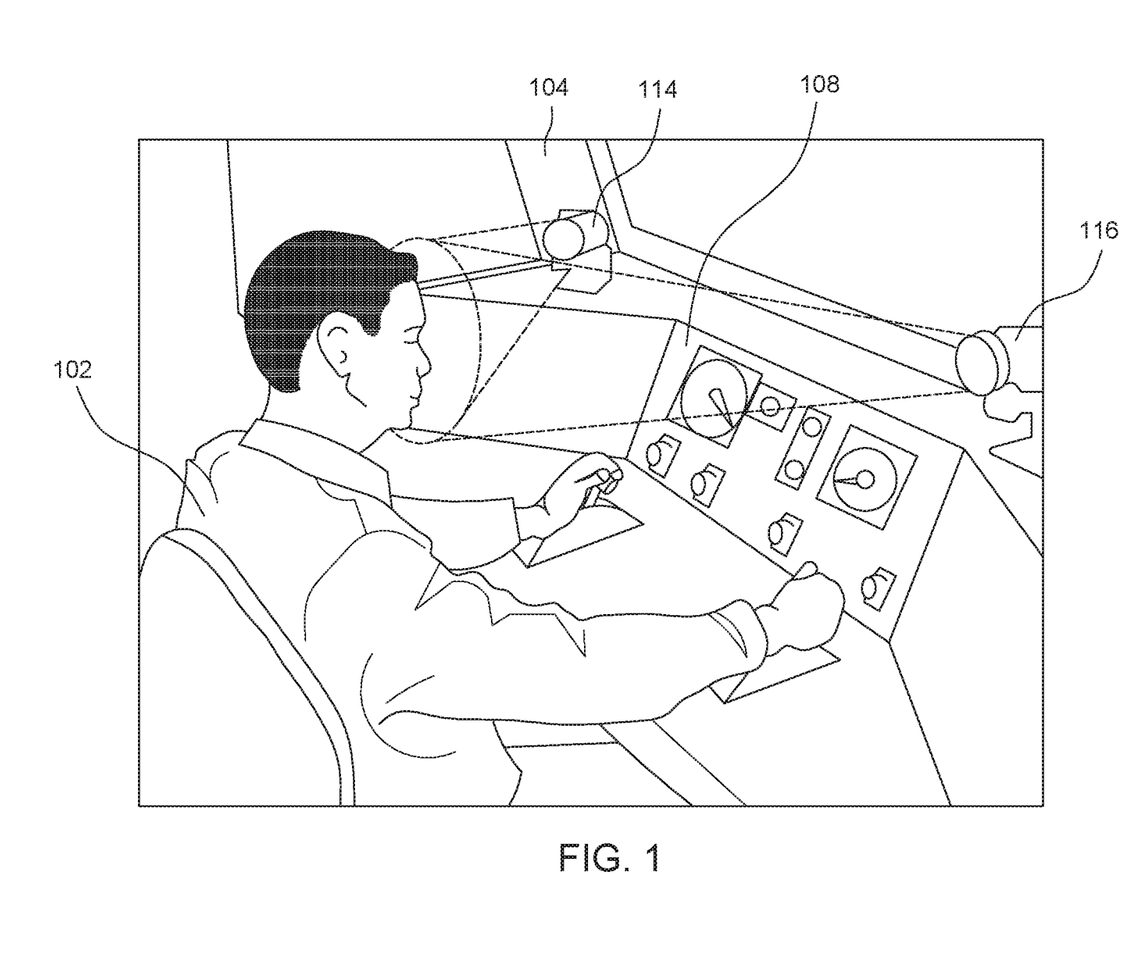
FIG. 1 is a schematic diagram of a control system for monitoring an operator within a vehicle in accordance with one embodiment.
Figure 2:
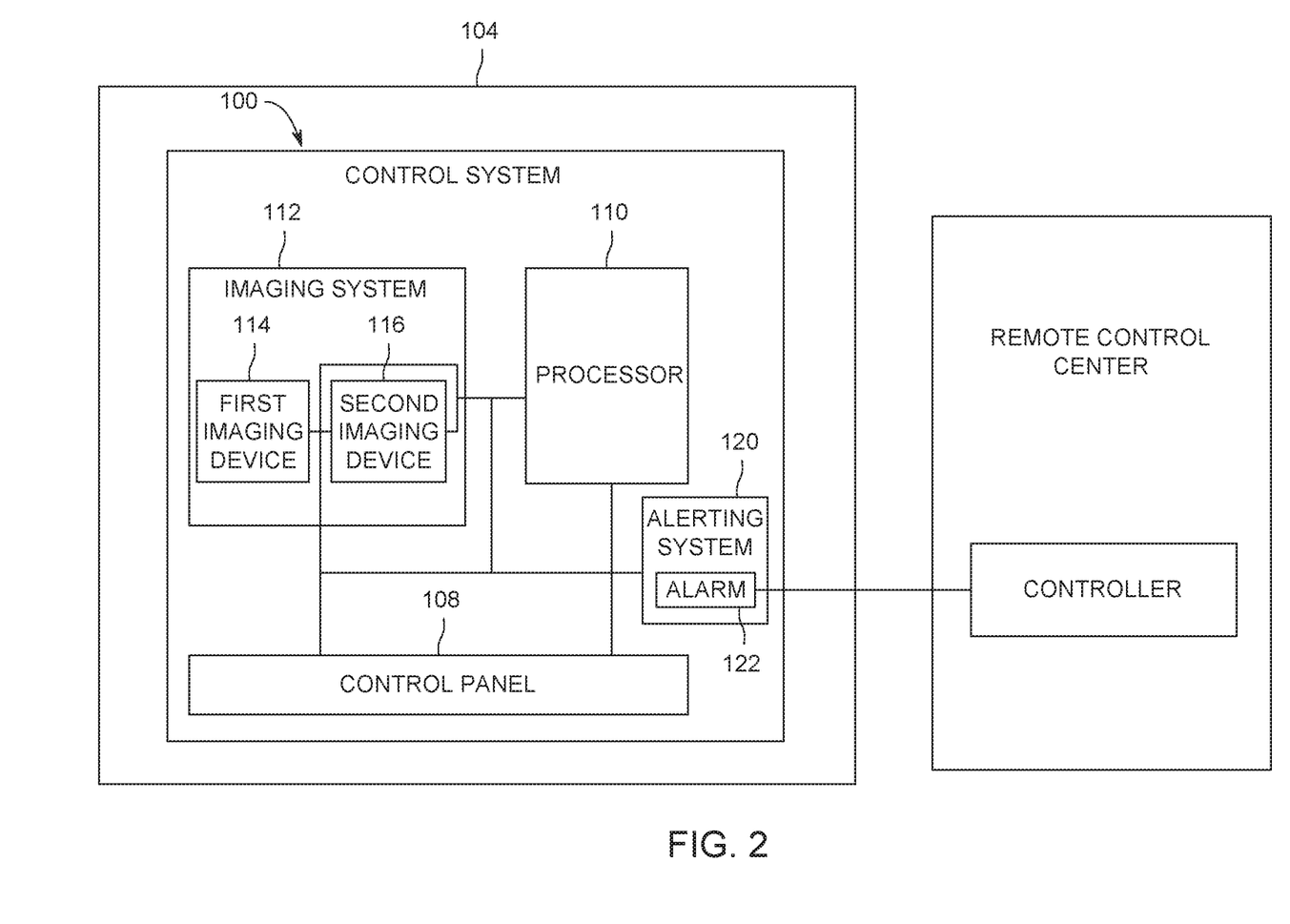
FIG. 2 is a schematic diagram of the control system of FIG. 1.

FIGS. 1 and 2 are schematic diagrams showing features of one embodiment of a control system 100 for monitoring an operator 102 of a vehicle 104. In this embodiment, the vehicle 104 is a locomotive. Optionally, the vehicle 104 may be another type of vehicle, such as an automobile, a truck, a bus, a marine vessel, an aircraft, a mining vehicle, or another type of off-highway vehicle (e.g., a vehicle that is not designed and/or is not legally permitted for travel on public roadways). The vehicle 104 has a controller 108 used by the operator 102 for controlling the vehicle 104 based on inputs of the operator 102. The controller 108 can represent hardware circuitry that includes and/or is connected with one or more processors (e.g., one or more microprocessors, field programmable gate arrays, and/or integrated circuits) that generate control signals that are communicated to propulsion systems, brake systems, and/or output devices to control movement and other operations of the vehicle. The control system 100 can be the control system for the vehicle 104 or can be in communication with and interact with the control system of the vehicle 104. The control system 100 also includes one or more processors 110 configured to store, receive and transmit data, including but not limited to 3P model, historical data and real-time data. The control system 100 is configured to make calculations utilizing algorithms and store look up tables therein to generate 3P outputs related to the operator 102.

An imaging system 112 is also part of the control system 100 and is in communication with the one or more processors 110 to provide real-time data related to the operator 102 to the one or more processors 110. The imaging system 112 in one embodiment includes a first imaging device 114 that is a RGB camera and continually records digital images of the operator 104. The first imaging device 114 generates pixel based data in real-time that is continuously communicated to the one or more processors 110. In this embodiment a second imaging device 116 is also provided that is a thermal camera. Specifically, the thermal camera generates thermal based data related to the operator 102 in real-time that is also continuously communicated to the one or more processors 110.

As both reflective and IR images contain information above and below the skin surface, based on the feature extraction one or more processors use a 3P model to obtain operator health parameters such as heart rate, respiration rate, fatigue and drowsiness levels and operator based physical indicators. The psychophysiological features obtained from blood volume waveform extracted from imaging devices such as RGB device are: blood oxygen saturation, tidal respiration rate, a Poincare Plot of peak-to-peak pulse dynamics, a pulse harmonic strength, power in harmonics of cardiac frequencies, heart rate variability, pulse rate, pulse amplitude, statistical features and key salient transition points on the waveform. The control system thus uses the RGB and additionally thermal imaging system to extract various physical cues/features such as specific micro-expression associated with nuanced muscle movement, macroexpressions, eye closure (blink-rates), head nodding, and yawning. Motion signatures are obtained by computing space-time corners or interest points. The physical and psychophysiological features from the imaging system computed in one of the processors are then used in the 3P model to determine fatigue and drowsiness levels. While some of the psychophysiological features have health information, in this manner the operator is monitored for both 3P as well as health conditions for determining attentiveness of the operator at controlling the vehicle.

The RGB and thermal image of a subject face are taken simultaneously with the co-located imaging devices of the imaging system. Then, a pre-computed transformation (a homography) is used to warp the thermal image onto the RGB image. This results in a new joint image where each pixel has R, G, B, and T values. The production of such imagery allows subsequent algorithms to make determination related to alerting the operator and operating the vehicle.

Image alignment is then achieved via forward and back projection. For example, given a stream of RGBT images, facial landmarks such as the corners of the eyes and mouth as well as the contour of the face is automatically fitted to each image. This allows for a warping of the RGBT image into a canonical frontal view. In this manner the imagery is normalized. Therefore, pixels from different normalized images are assumed to be in correspondence.

In addition to the analysis of images in isolation, temporal features such as optical flow are incorporated directly into the image representation. In addition, a Bayesian framework is constructed by considering the probability of observing a given facial cue that have been observed during prior observations within the historical data. In particular, full facial regions are taxonomized from thermal images into action units and subcutaneous temperature of the action units are extracted as thermal features. Other historical data such as physical anthropometric data and age are also utilized in determining operator health parameters and modeling.

An alerting system 120 is also part of the control system 100 and is in communication with the one or more processors 110 to alert the operator and control the vehicle based upon and responsive to the real-time data related to the operator 102 received by the imaging system. The alerting system includes an alarm 122 that can be part of the control panel 108 or remote from the vehicle and monitored by a third party. In one embodiment the alarm 122 is a flashing light and in another embodiment the alarm makes a sound or provides voice commands to the operator 102 to startle and wake up a drowsy, fatigued or sleeping operator 102. In yet another embodiment, the alarm 122 sends a message to the operator via the control panel 108 and the alarm can be reset by the operator 102 using the control panel 108 if a health condition detected or determined by the control system 100 is not problematic to the operator.

In another embodiment, the alerting system 120 is in communication with a remote control system that can be at a control center and operated or monitored by a third party. Upon receiving communication from the alerting system 120 of a potential health and/or alertness condition of an operator, the third party can contact the operator 102 directly or monitor the vehicle remotely to ensure proper operation of the vehicle. The alerting system 120 either automatically or through remote actuation also controls the vehicle 104 to brake the vehicle 104 and stop the vehicle 104 based upon the health related conditions of the operator monitored by the imaging system 112. The alerting system 120 may also provide prompts to the operator 102 such as math questions or otherwise to attempt to gather additional health information regarding the operator through requested operator inputs before braking or stopping the vehicle. Similarly, the alerting system 120 can increase cognitive action through requested cognitive inputs such as solving simple problems to prevent sleepiness, drowsiness and fatigue prior to stopping the vehicle. Alternatively, the alerting system 120 can make recommendations for the operator of the vehicle again to prevent sleepiness, drowsiness and fatigue, to combat cognitive and health related conditions, or to ensure the attentiveness of the operator.

Thus, the control system utilizes the parameters provided in historical data, including a 3P model such that when the imaging system is monitoring an operator in real-time, the information received by the imaging system is used to compute physical and psychophysiological features. Once the features are computed, a 3P model is executed in real-time to determine whether an operator is fatigued, sleepy, sleeping, stressed, under duress, incapacitated, distracted or the like. Responsive to the real-time results from 3P features and output of 3P model, the control system can alert the operator, remote third party or both with an alarm or can operate the vehicle through braking or stopping the vehicle depending upon the 3P and/or health conditions monitored by the control system.

Figure 3:
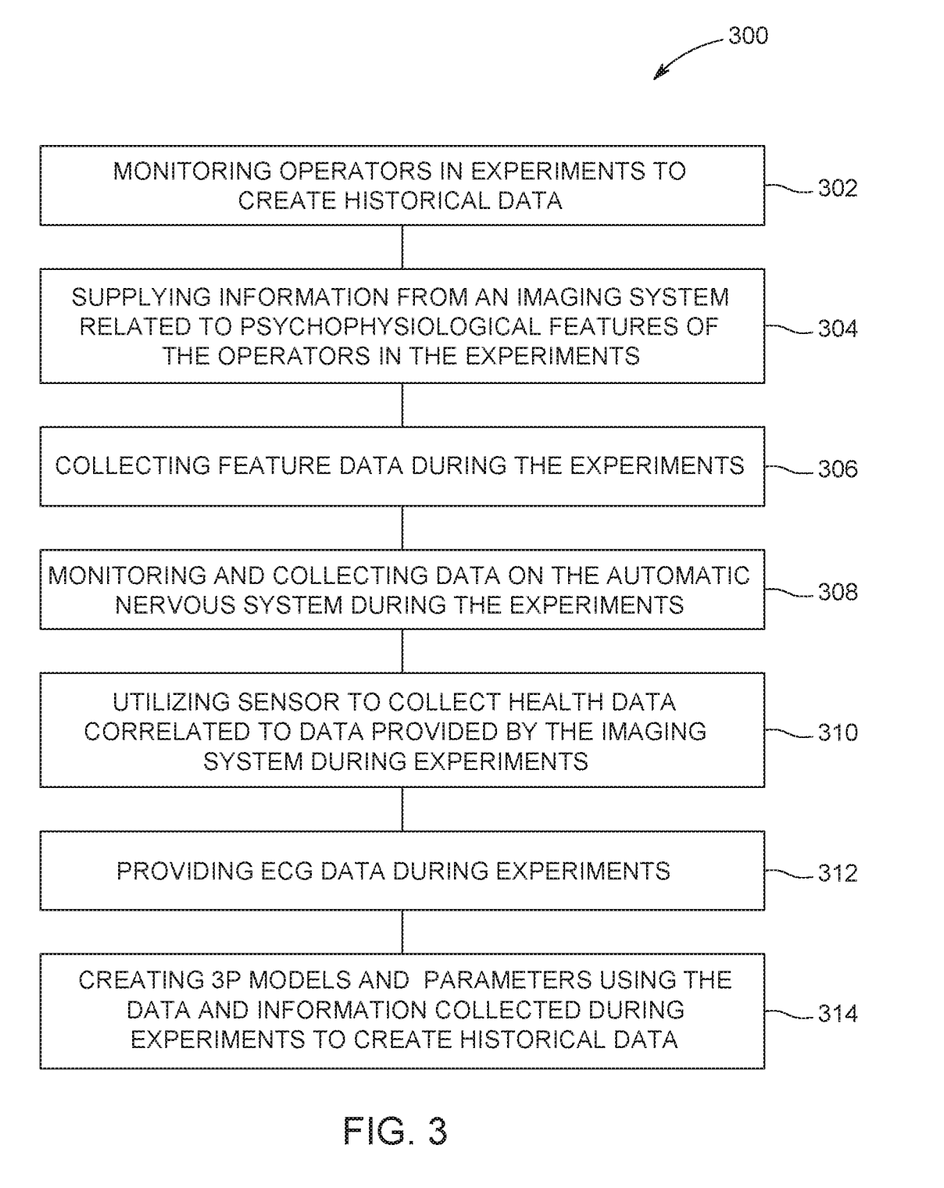
FIG. 3 illustrates a flow chart of a method of forming historical data for a control system.

FIG. 3 illustrates a flowchart of one embodiment of a method 300 of forming historical data and a 3P model to be used by the control system for monitoring the operator. At 302, in experiments, operators operating a vehicle are placed under a similar stressed environment in a controlled setting (e.g., a locomotive simulator) and are monitored with both an imaging system and physical body-worn sensors, including but not limited to electroencephalographic (EEG), photoplethysmographic (PPG), videoplethysmographic (VPG), electrocardiographic (ECG), ballistocardiographic (BCG), electromyographic (EMG), phonocardiographic (PCG), galvanic skin response (GSR), transcranial Doppler (TCD) sonography, and functional near infrared (fNIR) signals. The sensors can be passive or non-passive, and measurements are taken simultaneously with the images from the imaging system, including, but not limited to thermal images and digital images of the operator. To obtain a 3P model from the experimental data, the data is converted to meaningful features that correlate to physical and psychophysiological features. These features are used in a data driven parameterized mathematical model to estimate fatigue and drowsiness scores among other parameters to provide historical data for the control system. A well-known feature engineering methodology is incorporated to extract well-correlated features from the imaging devices to psychological indicators such as power spectrum in delta, theta, alpha, beta, and gamma bands, which indicates fatigue and drowsiness.

At 304, psychophysiological features extracted from contactless sensors are also supplied by the imaging system during the experiments used to create the historical data. Both reflective and IR video images contain information above and below the skin surface, and their spatial relations are useful for detecting psychophysiological features. In general terms, psychophysiological features that can be obtained from blood volume (BV) waveform, includes, but is not limited to tidal respiration rate, peak-to-peak dynamic periods, a pulse harmonic strength, power in harmonics of cardiac frequencies, heart rate variability (HRV), pulse rate, pulse amplitudes, statistical features, key salient transition points on the waveform, and the like.

At 306, during the experiments to create the historical data for the control system, the feature data collection, additional knowledge-based, shallow, and deep learning features are similarly collected and engineered. For example, a blood volume (BV) pulse signal is obtained from facial RGB videos. This is accomplished either by using model-based removal of signals due to specular mirror-like reflections from the skin surface or by post-processing using multi-band physiologic filters. The respiration rate is obtained from videos using one of three approaches; facial videos from blood volume waveform, measurement of motion-induced respiration, and nasal air flow with thermal images.

The HRV quantifies fluctuations in the interval between heartbeats, attributed to the continuous changes in the vago (parasympathetic)-sympathetic balance. In this manner the autonomic nervous system (ANS) is extracted from sensors at 308. The ANS regulates functions of internal organs and is one of the psychophysiological features used as historical data for obtaining the 3P models used by the control system. As an example of how monitoring the interval between heartbeats can be used to monitor an operator, if the monitored sympathetic tone is more dominant, it increases the heart rate, puts the body in "fight-or-flight response," a physiological reaction that occurs in the presence of something that is stressful, terrifying—either mentally or physically. Alternatively, and in opposite, increased parasympathetic stimulation lowers the heart rate, resulting in low energy and a desire to be at rest. Therefore, an indicator of feeling tired and drowsy as is the case after a meal is presented. While, HRV has historically been obtained from ECG and contact PPG signals; an operator or individual is monitored to provide historical data such that the RGB and T data is utilized to determine such fluctuations. Alternatively, HRV statistics can be extracted from BV waveform, again based on data collected from an imaging system. Thus, many methods can be used to utilize the imaging system to provide historical data for modeling related to the health of the operator.

Alternatively, historical data for the control system is created by utilizing sensors, such as the contact-PPG, that provides a much cleaner BV waveform, pulse rate, respiration rate, and HRV that are correlated to those obtained from the imaging device outputs at 310. At 312, ECG data is also used to provide data for modelling and is used to confirm PPG measurements. Similarly, EEG recordings show changes correlated with cognition (fatigue and drowsiness). A frequency spectrum of EEG signals is typically divided into five groups: delta signals (<4 Hz) being the slowest waves are usually correlated with sleep; theta signals (4-7 Hz) are associated with drowsiness; alpha waves (7-15 Hz) are related to relaxation; beta waves (15-30 Hz) are mostly related to active thinking and a high-level of alertness; gamma signals (>30 Hz) are related to perception of external stimuli such as sound and images with a high cognition level. Thus, power spectrum in delta, theta, alpha, beta, and gamma bands act as good indicators of psychophysiological activities (i.e., ground truth) for developing the model for estimating state-of-mind using features extracted from the imaging system while operating the train.

Once features are engineered, a subset of, well-correlated features from the imaging system are compared to psychological indicators to construct an input-output model to be used as historical data at 314. The vector of 3P features is fit to a plurality of models. The 3P model is an input/output (I/O) model which receives a vector of physical and physiological features and generates, as output, psychological quantities. The 3P model is comprised of a plurality of fitting functions, and may be developed with basis functions, which are aggregated to obtain outputs. Parameters of the model are fitted to a training data set using conventional least squares or sparse optimization methods.

Figure 4:
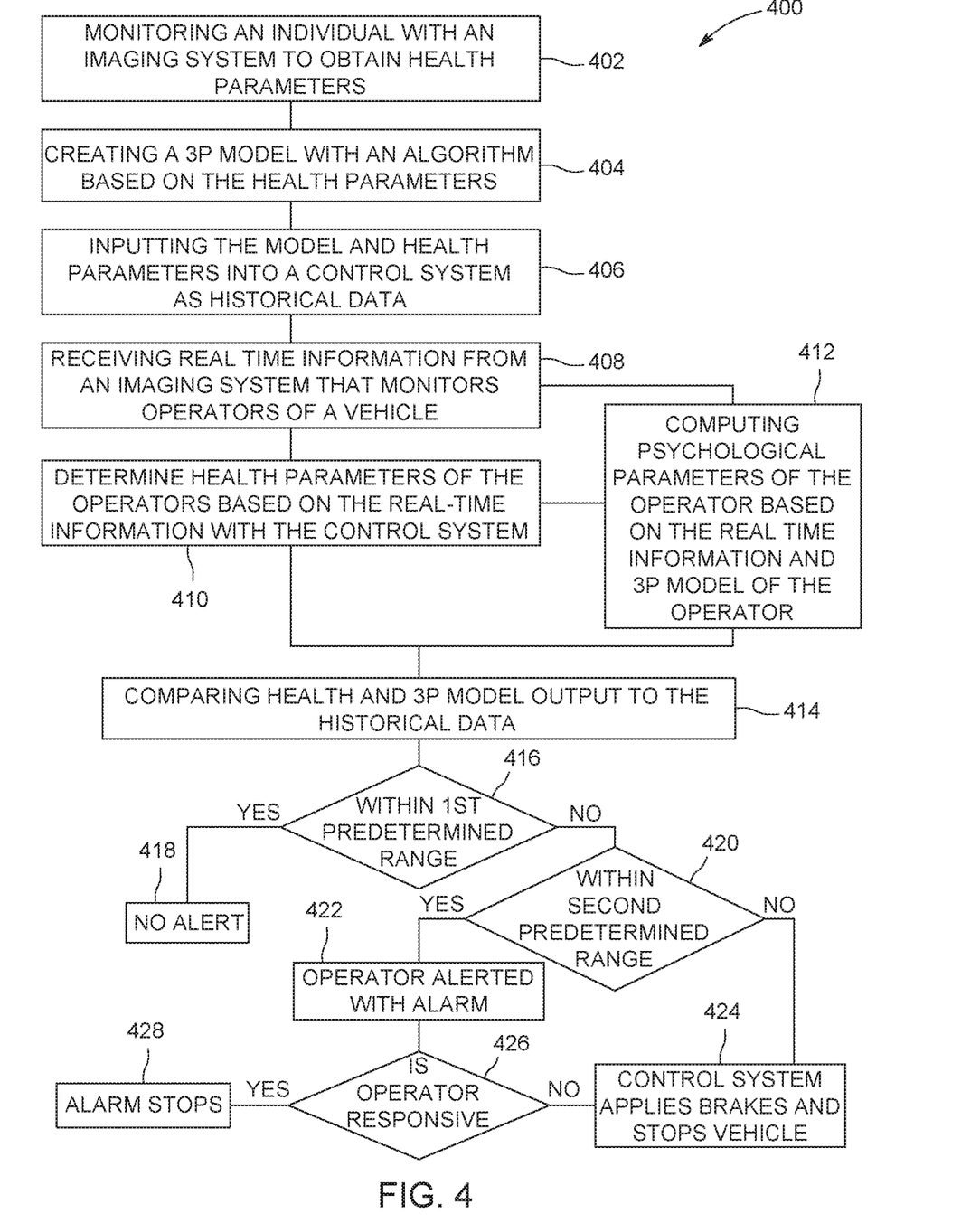
FIG. 4 illustrates a flow chart of a method for monitoring an operator of a vehicle.

FIG. 4 shows a method for alerting an operator 400. At 402, an individual is monitored by an imaging system and sensors during conditions similar to operating a vehicle to obtain physical, physiological and psychological parameters under predetermined stress conditions. The imaging system can include a first imaging device that is a RGB digital camera and a second imaging device that is a thermal camera. Other imaging devices described above can also be used during the creation & use of 3P model. At 404, the physical, and psychological parameters are utilized with an algorithm to form a 3P model of an operator. At 406, the model and health based parameters are inputted into a control system of a vehicle as historical data.

At 408, the control system receives real-time information from an imaging system that monitors an operator of the vehicle. The imaging system can include a first imaging device that is a RGB digital camera and a second imaging device that is a thermal camera. In other embodiments, other imaging devices are utilized as discussed above. At 410 the control system determines physical, physiological and psychological features or parameters from the real-time information received from the imaging system. Optionally, at 412, the control system uses these features to compute health and psychological (fatigue and drowsiness) conditions from 3P model of the operator based upon the real-time information received from the imaging system or from the physical, physiological and psychological parameters determined by the control system.

At 414, the real-time 3P model output and health parameters, are used to compare the health and psychological condition of the operator to the inputted historical data. At 416, if during the comparison at 414 the output parameters of 3P model fall within a first pre-determined range, then no alert is provided at 418. At 420, if during the comparison at 414 the parameters or output of 3P model do not fall within the first pre-determined range, a decision is made whether they fall within a second pre-determined range that indicate an operator health related issue and is presented to the control system which then alerts the operator by actuating an alarm at 422. Examples of such operator health related issues that would cause a parameter or the output of 3P model to fall with the second pre-determined ranges includes, but is not limited to, head nodding indicating fatigue or drowsiness, head or eye movement away from the front of the vehicle indicating distracted driving, increased heart rate, irregular beats as in atrial fibrillation or breathing indicating potential sickness or emergency condition, or the like.

At 420, if the parameters or output of 3P model do not fall within the second pre-determined range that indicates a serious operator health related issue and the control system brakes or stops the vehicle at 424. Examples of such operator health related issues include extreme increase in heart rate, irregular heartbeats, stoppage of breathing, extreme fluctuations in facial temperature, delayed cognitive responses or other indication that the operator is incapacitated, intoxicated or experiencing a severe health condition. Similarly, if the alarm is actuated at 422 the operator must actuate the control panel to shut off the alarm at decision point 426. If the operator is responsive the alarm stops at 428. If the operator is not responsive the control system brakes or stops the vehicle again at 424.

As an example of how the method of FIG. 4 works, after the physical, physiological and psychological parameters under predetermined stress conditions in a controlled environment are obtained and/or the operator model determined, the imaging system continuously monitors the operator of a vehicle using real-time data. In this example a RGB digital camera provides information that the operator starts to blink their eyes significantly more often than compared to the physical, physiological and psychological parameters provided for in the historical data and/computed from the 3P model using real-time data. The imaging system also provides that the operator's eyelids remain closed longer than a typical blink also within the historical data. As a result of these conditions or parameters, the control system actuates its alarm to alert the driver that he is becoming fatigued. A message is also communicated remotely to an operations center to alert a third party that the driver is fatigued.

As yet another example, both physical and psychophysiological features from the imaging devices are extracted from real-time data and used as input to the multivariate 3P model to generate the output such as the psychological state of the operator (i.e., fatigue and drowsiness levels). If the fatigue and drowsiness levels exceed the predetermined limit as indicated in the historical data, then the control system actuates its alarm to alert the driver that he is becoming fatigued.

As another example, a thermal camera of the imaging system detects that the face of the operator becomes flushed, indicating an increased heart rate. Based on the sudden increase of heat of the operator the control system alerts a remote operations center that the operator is experiencing an increased psychophysiological state (e.g., heart rate or heart rate variability). An individual at the remote operations center then contacts the operator to check their status while the alarm is actuated by the control system and the operator is requested to provide input into the control system. When the operator is unresponsive and unable to provide input, the control system stops the vehicle.

In yet another example, the imaging system indicates that the operator is having problems swallowing. The control system alerts the operator that a potential health condition may be present. If the operator merely had a tickle in their throat, he/she can actuate the control panel to address the alert and no further action of the control system occurs.

In another example, the imaging system monitors an operator's head gaze direction to provide data and information related to operator focus and attentiveness. By tracking and analyzing gaze direction, the frequency of changes in operator focus is inferred. Large motion signatures are then used to isolate region of interests (ROIs) that contain motion and less desirable for extracting psychophysiological features. If the operator remains properly focused, the control system allows for normal operation of the vehicle without use of the alarm.

While the control system is described as utilized to monitor an operator of a locomotive, numerous other applications exist. In one example the control system can be used to improve overall safety when an individual is carrying out critical tasks such as driving vehicles or piloting aircraft. The control system in one example is used to perform "fit-to-work" assessments, to alert administration of possible changes in personnel mental status in daycare centers and hospitals, or to help caregivers interact more effectively with children of special needs (e.g., autistic). All uses are contemplated and do not fall outside the scope of this disclosure.

In one embodiment, a control system is provided. The control system has one or more processors configured to determine physical, physiological or psychological changes of an operator of a vehicle without requiring intervention of the operator. The one or more processors are also configured to, responsive to the 3P changes of the operator of the vehicle that are determined indicating that the operator is inattentive to control of the vehicle, alert the operator. The one or more processors are also configured to receive information from an imaging device and determine the 3P changes of the operator based on the information received from the first imaging device. In one embodiment, the first imaging device is a digital RGB camera. In another embodiment the imaging device is one of a reflected near infrared (NIR) camera or a shortwave infrared (SWIR) camera. In yet another embodiment the imaging device is based on an ultra-wide band microwave imaging technology. Multi and hyperspectral cameras are also considered feasible embodiments.

In one embodiment the one or more processors are configured to receive information from a second imaging device and determine thermal changes related to the operator based on the information received from the second imaging device. In one embodiment the second imaging device is a thermal camera such as a midwave infrared (MWIR) or a longwave infrared (LWIR) camera which is capable of collecting emitted waves. In another embodiment the one or more processors are configured to combine the information from the first imaging device and the information from the second imaging device to determine the 3P changes of the operator. In yet another embodiment the information from the first imaging device and the information from the second imaging device are both related to the face of the operator.

In one embodiment, the one or more processors are configured to alert the operator by utilizing an alarm. In another embodiment, the one or more processors are configured to alert the operator by braking the vehicle.

In yet another embodiment, the one or more processors are configured to receive information from a first imaging device related to physical, physiological and psychological parameters of the operator and to use a 3P model from historical data to produce psychological output such as fatigue and drowsiness levels based on these parameters. In another embodiment the physical, physiological and psychological parameters are measured by one or more of, electroencephalographic (EEG), photoplethysmographic (PPG), electrocardiographic (ECG), ballistocardiographic (BCG), electromyographic (EMG), phonocardiographic (PCG), galvanic skin response (GSR), transcranial Doppler (TCD) sonography, or functional near infrared (fNIR) signals, on a human in a controlled setting.

In one embodiment, a method is provided that has steps including determining 3P changes of an operator of a vehicle and responsive to the 3P changes of the operator of the vehicle that are determined indicating that the operator is inattentive to control of the vehicle, alerting the operator with an alarm. In an additional embodiment an additional step of recording the operator with a first imaging device to collect information related to the operator used to determine the 3P changes of the operator is also provided. In yet another embodiment, provided is the additional step of recording the operator with a second imaging device to collect information related to the operator used to determine the additional 3P changes of the operator. In another embodiment, the additional step of monitoring the operator with at least one sensor to collect information related to the operator used to determine the 3P changes of the operator is provided.

In yet another embodiment, an additional step provided is using the 3P changes of the operator along with historical data to determine when to alert the operator of the vehicle with the alarm. In another embodiment, the historical data is a predetermined threshold for health parameters and fatigue and drowsiness levels.

In one embodiment, a control system is provided that has one or more processors configured to determine 3P changes of an operator of a vehicle and the one or more processors also configured to, responsive to the 3P changes of the operator of the vehicle that are determined indicating that the operator is inattentive to control of the vehicle, brake the vehicle. In another embodiment, the one or more processors also are configured to first alert the operate responsive to the 3P changes of the operator and then brake the vehicle based on a lack of response by the operator to the alert.

In one embodiment, the one or more processors also are configured to receive information from at least one imaging device monitoring a health parameter of the operator. In another embodiment, the one or more processors also are configured to receive information from a digital imaging device related to the health parameter of the operator. In yet another embodiment, the one or more processors also are configured to receive information from a thermal imaging camera related to the health parameter of the operator.

As used herein, an element or step recited in the singular and proceeded with the word "a" or "an" should be understood as not excluding plural of said elements or steps, unless such exclusion is explicitly stated. The phrase 'imaging device' is used to represent a device capable of producing 2D array image frames over time by capturing electromagnetic waves. These waves could be emitted from the body or radio/microwaves or visible/infrared waves reflected from the body. Images may come sequentially or may be reconstructed off-line outside the device from reflected signals as in the Ultra Wide Band mid-microwave or radar or depth measuring devices. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A control system comprising:
   one or more processors configured to receive a first image from a first imaging device and determine physical, physiological or psychological changes of an operator of a vehicle without requiring intervention of the operator based on the first image received from the first imaging device; and
   the one or more processors also configured to alert the operator responsive to the physical, physiological or psychological changes of the operator of the vehicle indicating that the operator is inattentive to control of the vehicle;
   wherein the one or more processors are configured to receive a second image from one or more of a thermal imaging device, a midwave infrared (MWIR) camera, or a long wave infrared (LWIR) camera, and determine thermal changes related to the operator based on the second image;
   wherein the one or more processors are configured to determine the physical, physiological or psychological changes of the operator using a new joint image that is generated by warping the second image onto the first image using a homography; and
   wherein one or more pixels of the new joint image of the operator has red (R), green (G), blue (B), and thermal (T) values.

2. The control system of claim 1, wherein the first imaging device is one or more of a digital camera comprising a detector array with one of red, green and blue wavelengths, a near infrared (NIR) camera, a short-wave infrared (SWIR) camera, a mid-microwave ultra-wide-band device, or a depth measuring camera.

3. The control system of claim 1, wherein the first image from the first imaging device and the second image from the thermal imaging device are both of a face of the operator.

4. The control system of claim 3, wherein the one or more processors also are configured to determine a probability of observing a facial cue.

5. The control system of claim 1, wherein the one or more processors are configured to alert the operator by actuating an alarm.

6. The control system of claim 1, wherein the one or more processors are configured to alert the operator by automatically engaging a brake of the vehicle.

7. The control system of claim 1, wherein the one or more processors are configured to form a model of the operator related to physical, physiological and psychological parameters of the operator based on the physical, physiological or psychological changes of the operator or a combination of the physical, physiological or psychological changes of the operator.

8. The control system of claim 7, wherein the physical, physiological and psychological parameters are measured by one or more of an electroencephalographic (EEG) device, a photoplethysmographic (PPG) device, an electrocardiographic (ECG) device, a ballistocardiographic (BCG) device, an electromyographic (EMG) device, a phonocardiographic (PCG) device, a galvanic skin response (GSR) device, a transcranial Doppler (TCD) sonography device, or functional near infrared (fNIR) signals, on a human in a controlled setting.

9. The control system of claim 1, wherein the one or more processors also are configured to warp the new joint image into a canonical frontal view.

10. The control system of claim 1, wherein the one or more processors also are configured to:
 determine the operator is incapacitated based on the physical, physiological or psychological changes of the operator determined; and
 stop the vehicle responsive to determining the operator is incapacitated.

11. The control system of claim 1, wherein the one or more processors also are configured to:
 responsive to the physical, physiological or psychological changes of the operator of the vehicle that are determined indicating that the operator is inattentive to control of the vehicle, alert a remote operations center.

12. The control system of claim 1, wherein the physical, physiological or psychological changes of the operator include eye movement away from a front of the vehicle.

13. A method comprising:
 receiving a first image from a first imaging device;
 determining physical, physiological or psychological changes of an operator of a vehicle based on the first image received from the first imaging device;
 alerting the operator responsive to the physical, physiological or psychological changes of the operator of the vehicle indicating that the operator is inattentive to control of the vehicle;
  receiving a second image from one of a thermal imaging device, a midwave infrared (MWIR) camera, or a long wave infrared (LWIR) camera, and determine thermal changes related to the operator based on the second image received from the thermal imaging device;
  determining the physical, physiological or psychological changes of the operator using a new joint image that is generated by warping the second image onto the first image using a homography; and
  wherein one or more pixels of the new joint image of the operator has red (R), green (G), blue (B), and thermal (T) values.

14. The method of claim 13 further comprising the step of recording the operator with a first imaging device to collect information related to the operator used to determine the physical, physiological or psychological changes of the operator.

15. The method of claim 13 further comprising the step of comparing the physical, physiological or psychological changes of the operator to historical data to determine when to alert the operator of the vehicle with the alarm.

16. The method of claim 15 wherein the historical data is a model.

17. The method of claim 15 wherein the historical data is a predetermined threshold for health parameters and fatigue and drowsiness levels.

18. A control system comprising:
 one or more processors configured to determine physical, physiological or psychological changes of an operator of a vehicle;
 the one or more processors also configured to brake the vehicle responsive to the physical, physiological or psychological changes of the operator of the vehicle indicating that the operator is inattentive to control the vehicle;
 wherein the one or more processors are configured to receive a first image from a first imaging device and determine the physical, physiological or psychological changes of the operator based on the first image;
 wherein the one or more processors are configured to receive a second image from one or more of a thermal imaging device, a midwave infrared (MWIR) camera, or a long wave infrared (LWIR) camera, and determine thermal changes related to the operator based on the second image;
 wherein the one or more processors are configured to generate a new joint image by warping the second image onto the first image using a homography and to determine the physical, physiological or psychological changes of the operator on the new joint image; and
 wherein one or more of the pixels of the new joint image of the operator has red (R), green (G), blue (B), and thermal (T) values.

19. The control system of claim 18 wherein the one or more processors also are configured to first alert the operator responsive to the physical, physiological or psychological changes of the operator and then brake the vehicle based on a lack of response by the operator to the alert.

20. The control system of claim 19 wherein the one or more processors also are configured to receive information from at least one imaging device monitoring a health parameter of the operator.

21. The control system of claim 20 wherein the one or more processors also are configured to receive information from an imaging device that contains the health parameter of the operator.

* * * * *